US012584031B2

(12) United States Patent
Yadavalli et al.

(10) Patent No.: US 12,584,031 B2
(45) Date of Patent: Mar. 24, 2026

(54) METHOD FOR CONNECTION TO A RIGID OR FLEXIBLE DEVICE USING MULTIFUNCTIONAL INK

(71) Applicant: VIRGINIA COMMONWEALTH UNIVERSITY, Richmond, VA (US)

(72) Inventors: Vamsi Yadavalli, Richmond, VA (US); Sayantan Pradhan, Richmond, VA (US); Sudesna Chakravarty, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 67 days.

(21) Appl. No.: 18/690,446

(22) PCT Filed: Sep. 7, 2022

(86) PCT No.: PCT/US2022/042716
§ 371 (c)(1),
(2) Date: Mar. 8, 2024

(87) PCT Pub. No.: WO2023/038943
PCT Pub. Date: Mar. 16, 2023

(65) Prior Publication Data
US 2024/0376332 A1      Nov. 14, 2024

Related U.S. Application Data

(60) Provisional application No. 63/242,716, filed on Sep. 10, 2021.

(51) Int. Cl.
*C09D 11/52* (2014.01)
*C09D 11/037* (2014.01)
*G01N 33/543* (2006.01)

(52) U.S. Cl.
CPC ............ *C09D 11/52* (2013.01); *C09D 11/037* (2013.01); *G01N 33/54326* (2013.01); *G01N 33/54346* (2013.01)

(58) Field of Classification Search
CPC .................. C09D 11/52; C09D 11/037; G01N 33/54326; G01N 33/54346; C08K 2201/01
See application file for complete search history.

(56) References Cited

U.S. PATENT DOCUMENTS 5,264,157 A * 11/1993 Bidan .................... H01B 1/127
524/779
2004/0009346 A1* 1/2004 Jang ...................... B82Y 10/00
423/445 B (Continued)

FOREIGN PATENT DOCUMENTS

JP          S61254669 A  * 11/1986
WO      2021/092532 A1     5/2021

*Primary Examiner* — Mark Kopec
*Assistant Examiner* — Jaison P Thomas
(74) *Attorney, Agent, or Firm* — WCF IP

(57) ABSTRACT

The technology is based on a conducting, ferromagnetic ink made from, in an aqueous suspension: conducting nanopolymers, ferromagnetic nanoparticles, an adhesion promoter and optionally, a surfactant and/or stabilizer. The ink is used to form reversible physical and electrical connections between e.g., rigid and flexible devices. In some aspects, the conducting nanopolymers are PEDOT:PSS (poly(3,4-ethylenedioxythiophene) polystyrene sulfonate) nanopolymers and the magnetic nanoparticles are iron oxide nanoparticles. The ink, which may be magnetic, is used to form solid, flexible, ferromagnetic conducting designs or nodes which may also be magnetic. The flexible, ferromagnetic conducting designs or nodes are used to form reversible magnetic electrical connections with devices such as potentiostats and data telemetry devices.

8 Claims, 16 Drawing Sheets

(56) References Cited

U.S. PATENT DOCUMENTS

| | | | |
|---|---|---|---|
| 2006/0083694 A1* | 4/2006 | Kodas | B01J 13/0095 |
| | | | 424/490 |
| 2018/0059100 A1 | 3/2018 | Fattah et al. | |
| 2020/0068752 A1* | 2/2020 | Badihi | C09D 7/61 |
| 2021/0277268 A1 | 9/2021 | Martin et al. | |

* cited by examiner

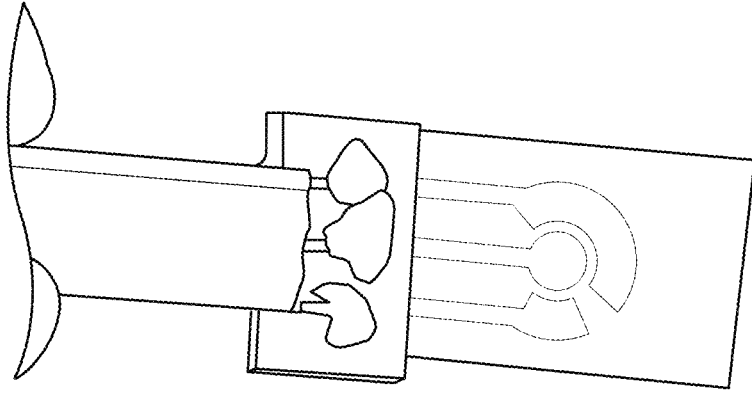
Fig. 11
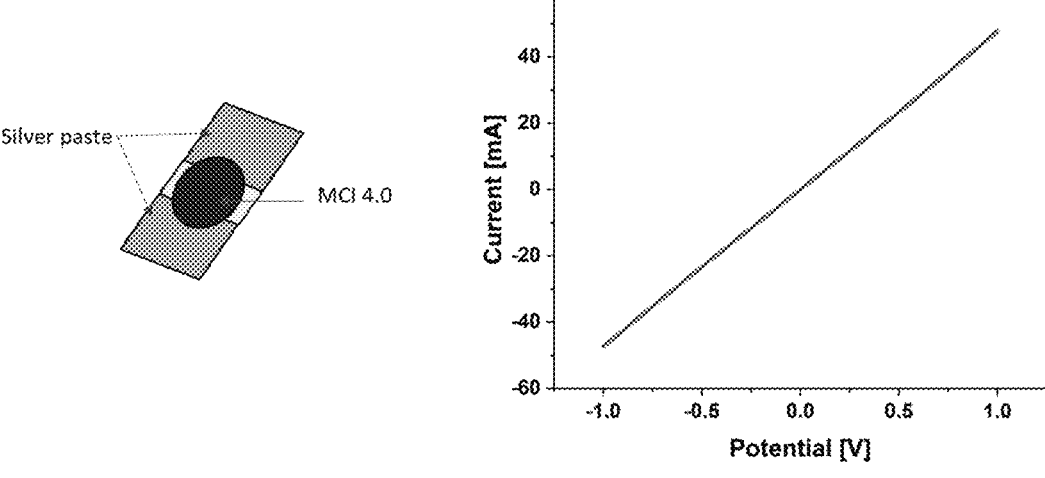
Figure 12A                    Figure 12B

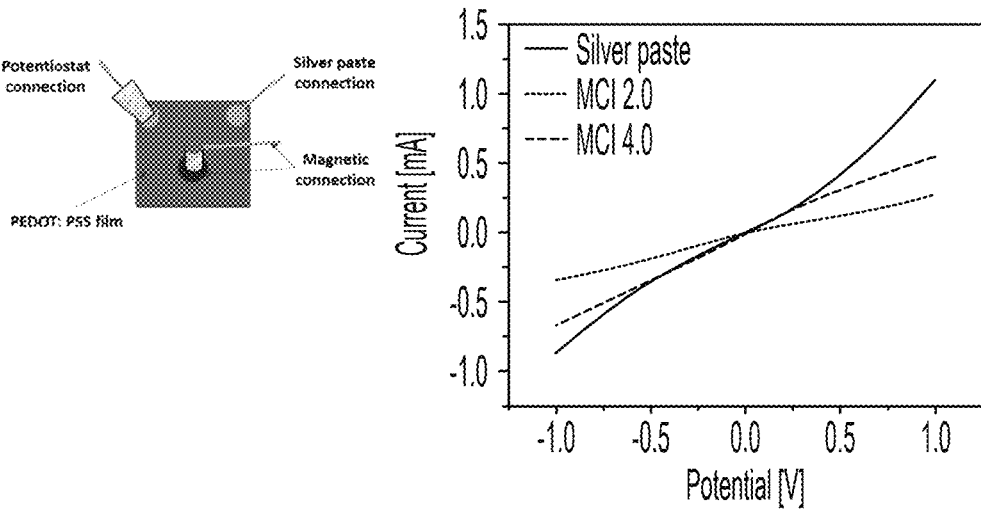
Figure 13A                    Figure 13B
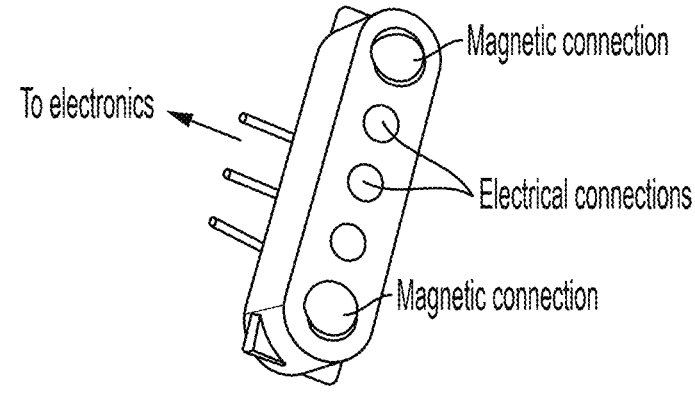
Figure 14A
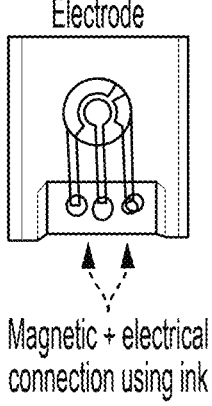
Figure 14B Magnetic connector To electronics Connection via contact

ON

OFF

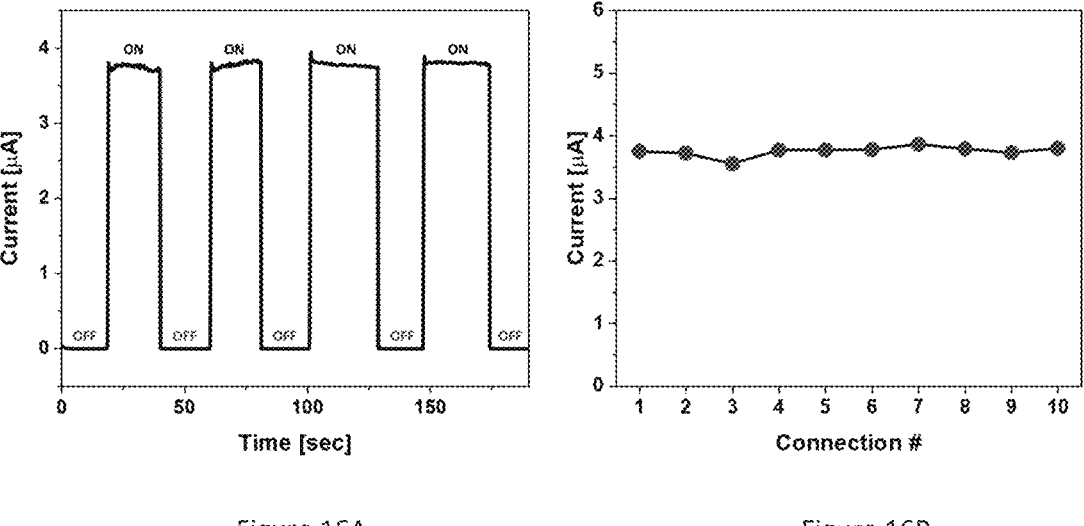
Figure 16A                                        Figure 16B
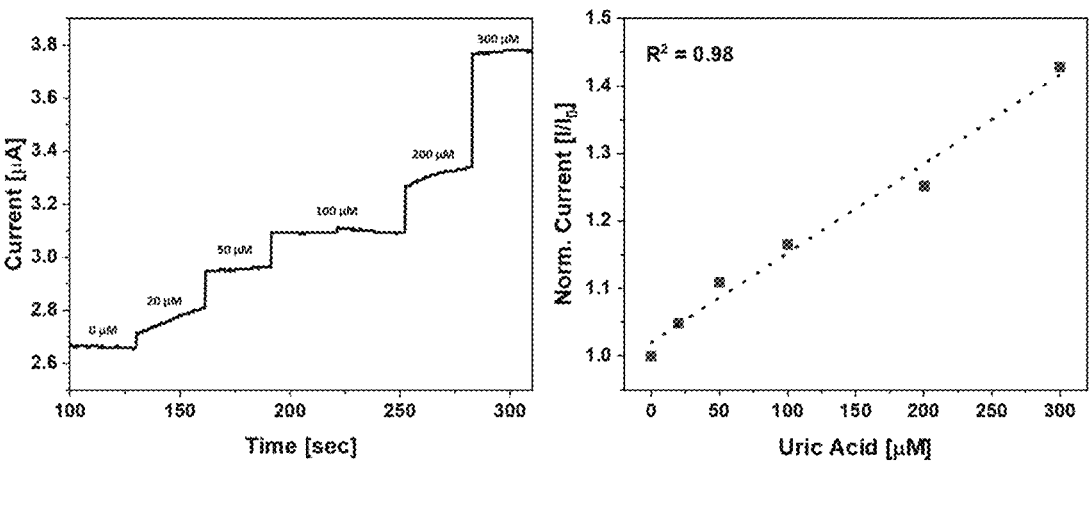
Figure 17A                                        Figure 17B

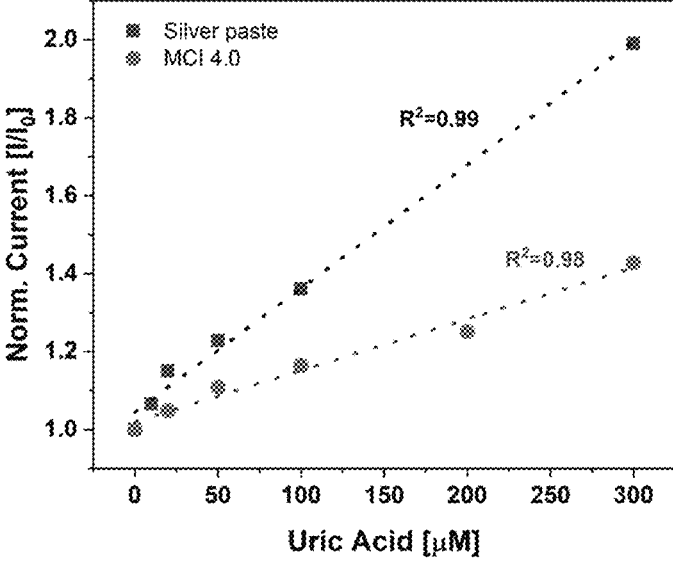
Figure 17C
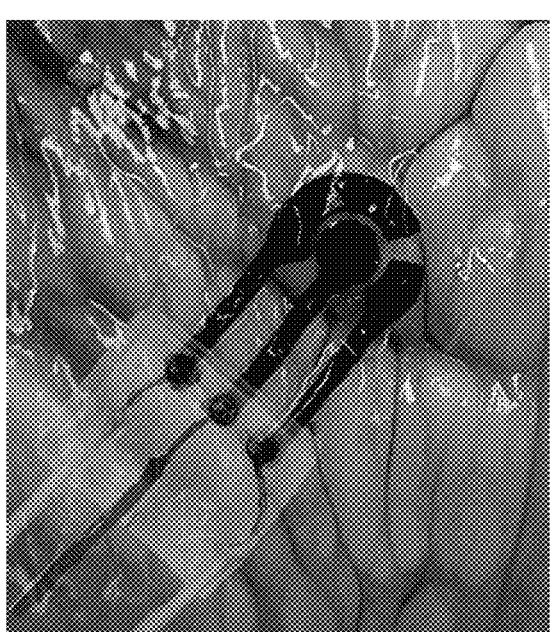
Figure 18A                 Figure 18B

METHOD FOR CONNECTION TO A RIGID OR FLEXIBLE DEVICE USING MULTIFUNCTIONAL INK

STATEMENT OF FEDERALLY SPONSORED RESEARCH AND DEVELOPMENT

This invention was made with government support under Grant Number 1704435 awarded by the National Science Foundation. The United States government has certain rights in the invention.

BACKGROUND OF THE INVENTION

Field of the Invention

The invention generally relates to transient physical (ferromagnetic and/or magnetic) and conducting (electrical) connectors made from ferromagnetic (and optionally magnetic), conductive ink, methods of making the connectors, and methods of using the connectors to reversibly connect electrical devices.

Description of Related Art

To form connections and inter-connects between electronic devices and power sources, or sensor-leads for use in biosensors and bioelectronics, various options are used. For instance, the connections are made using conducting pastes, adhesive conducting tapes, clamps, sockets, etc. Permanent connections may be made using soldering. These forms of connections are useful in rigid as well as flexible systems. However, the connections tend to suffer from various issues including, but not limited to:

mechanical mismatch between the components, particularly when one of the surfaces is flexible and the other is not;
 mechanical mismatch between the adhesive and the components, particularly when the components are soft materials/thin films. In cases of mechanical mismatch, the interface is vulnerable to stress and structural failure;
 requirement of force to make the connection (particularly in the case of adhesives), potentially resulting in damage during connection or disconnection;
 permanence of bonding (e.g., adhesives such as epoxies), precluding easy replacement;
 requirement of alignment of the connectors (e.g., male-female) prior to circuit formation.

Magnetic connectors are available for use in electronic devices and circuits to provide the mechanical connection (FIG. 1A). However, i) typically such connectors have a separate magnetic connection and the electrical connection is formed via direct contact or spring-loaded pins such as pogo pins; and ii) these connectors are useful primarily in rigid configurations.

There is a need in the art for improved electrical connections, especially easily reversible electrical connections in both flexible and rigid devices.

US patent application 20190333695 describes a direct writing method of producing a magnetic pattern on a substrate by extruding one or more filaments of a magnetic ink compound through a nozzle and curing the plurality of filaments using UV light and/or heat. However, there is no discussion of using a conducting polymer (the ink is formed from a photopolymer resin base and magnetic particles) or of making an electrical circuit.

US patent application 20190089087 discloses a connector and a connector assembly which is attached to a bendable object of interest such as clothing. The connector has a plate-shaped housing, electrically conductive contacts arranged on the housing, and a plurality of retainer members formed from a magnetic metal and arranged in the housing. When the connector is mated with a mating connector, the retainer members are attracted to a magnet of the mating connector to maintain the connection. When the connector is sewn onto clothing and mated with the mating connector, the electrically conductive pattern of the clothing and the conductor are electrically connected to each other.

US patent application 20180026393 describes devices that include magnets which are either inherently sufficiently electrically conductive and/or are coated with electrically conductive material to enable detachable, conductive, magnetic connections between devices. The magnets are attached to electrical traces, pads, or other conductive material in each of the parts of the system that are to be connected or disconnected. One of the devices may be a disposable or reusable device and can include a rigid and/or flexible circuit, such as a stretchable, flexible substrate with circuitry that can monitor a biological parameter. However, the emphasis is on disposable devices attached to the skin and electrically connected to processors and/or storage devices for processing and storing the information. Further, there is no mention of the magnetic connections being formed from a magnetic ink.

US patent application 201800264801 describes the deposition of a magnetic ink onto a portion of a substrate such that the amount of magnetic ink is divided into a plurality of individual sections that are spaced at substantially regular intervals. The individual sections may or may not have a common shape. The substrates can be used to form objects having a number of shapes and structures. However, there is no discussion of forming electrical connections.

US patent application 20170149171 discloses a system of connecting two or more communication devices each of which has an interface and a housing with a peripheral surface, and a connector. The devices are positioned at the interfaces through magnetic connectors which provide mechanical and electrical connection, e.g., for charging a device. However, there is no mention of making the magnetic connectors from magnetic ink, the arrangement of the magnets appears to be much more complex than in the present disclosure, and there is no mention of e.g., flexible sensors. The emphasis is instead on e.g., cell phones, speakers, etc.

Issued U.S. Pat. No. 6,322,620 discloses a thermoset conductive ink for use in through hole interconnections or similar electric and electronic applications to provide stable electrical connections. The conductive ink comprises a thermal curable resin system comprising an epoxy resin, a cross-linking agent and a catalyst, an electrically conductive material such as silver, copper or silver-coated copper and an organic solvent. The compositions thus differ from those of the present invention and are not described as magnetic or useful for making magnets.

Issued U.S. Pat. No. 6,030,229 describes as electromagnetic detachable connector which includes a pair of female and male connectors. Each of female and male connectors includes a movable section and a fixed section and a permanent magnet and an electromagnet are arranged at predetermined positions of the female and male connectors. An electromagnetic force on the permanent magnet causes the movable sections move in a direction so as to come closer to or farther away from each other, achieving high precision drive control for connection and disconnection. However, neither of the magnets is formed from magnetic ink.

Issued U.S. Pat. No. 7,771,624 teaches nanoparticles, conductive ink containing the nanoparticles, and a circuit line forming device using the conductive ink for forming micro circuit lines on a substrate. The nanoparticles include a ferromagnetic core (5 to 40 parts by weight) and a conductive layer surrounding the ferromagnetic core. The conductive ink provides electrical reliability by allowing a uniform distribution of nanoparticles when the ink is ejected onto a substrate. However, there is no discussion of forming magnets or of reversible magnetic electrical connections.

Issued U.S. Pat. No. 10,609,967 provides an electrically conductive magnetic snap fastener comprising male and female coupling elements for releasably coupling a first material to a second material. When the male and female fastening elements are magnetically coupled to each other, a conductive electrical path is formed. Exemplary uses include in wearable devices such as heart monitors to provide electrical connections to conduct electrical signals. However, in contrast to the present invention, the male and female fastening elements are required.

Issued U.S. patent Ser. No. 10/655,024 teaches a biodegradable supercapacitor system comprising a protein based flexible thin film substrate, patterned electrodes formed from a biocompatible conductive ink, and biocompatible gel electrolyte. The biocompatible conductive ink that is used may be the same as that described in the present invention (PEDOT:PSS plus an iron oxide). However, the ink is not used to form a magnet that provides a mechanism for a detachable, reversible electrical connection.

Japanese patent application JP2012209376A provides an iron oxide nanoparticle dispersion liquid which suppresses oxidization of a material which is likely to be oxidized (such as metal) when brought into contact with the material. The dispersion liquid contains an iron oxide particle of which the primary particle diameter is 100 nm or less and the secondary particle diameter is 500 nm or less, and a dispersion liquid comprising a polar solvent having at least one of an ester group and a sulfoxide group. The iron oxide particle is preferable selected from $\varepsilon$-FeO, $\gamma$-FeO, $\alpha$-FeO, and FeO. The application states that nanocomposite magnets magnetic recording media, or electromagnetic wave shields are produced using the iron oxide particle dispersion. However, no uses of the nanocomposite magnets are described and the composition clearly differs from that of the present invention, e.g., no conductive polymer is included.

International patent application WO2016/122405 teaches an electrical connector device, comprising a first component that is flexible comprising at least one first magnetic part and a first housing having a first contact surface, and a second component that is flexible and/or rigid comprising at least one second magnetic part and a second housing having a second contact surface The at least one first and the at least one second magnetic parts are complementarily positioned in the first and second housings, respectively, to enable coupling of the first and second contact surfaces through magnetic interaction; electricity and/or signaling data is conducted through the first and second magnetic parts when coupled. The magnetic parts couple securely because one is recessed and the other protrudes and engages with the magnet within the recess.

There is a need in the art for flexible, reversible connectors, e.g., for use to connect to biosensors and flexible devices or wearables.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

An embodiment of the invention provides a water-based multifunctional conductive ink (MCI) that includes a combination (mixture) of i) ferromagnetic nanoparticles and ii) electrically conductive nanoparticles which are nanopolymers. When the MCI is solidified (i.e., dehydrated or dried), a flexible solid composition is formed that is both conductive and ferromagnetic. At least about 95% of the water has been removed from the dehydrated flexible solid composition, e.g., at least about 95, 96, 97, 98 or 99% or more of the water has been removed. The ink itself and solid compositions made from the ink may or may not also be magnetic, i.e., the ferromagnetic nanoparticles may be, but are not necessarily, magnetic. A flexible solid composition formed from the MCI is capable of forming a temporary, reversible (transient) connection in contact with a magnetic surface which is part of and/or is electrically connected to an electronic device, for example, a sensor. The connection is both physical (magnetic) and conductive (electrical). In devices and systems comprising flexible conducting compositions according to embodiments of this invention can be formed e.g., between a solid flexible conducting composition made from the MCI and a rigid or flexible magnet that is part of a device. The connections are advantageously typically temporary and reversible, i.e., the surface of the flexible conducting composition can be attached to the surface of a magnet of a device, and then the two surfaces can be subsequently detached from each other by simply pulling, or alternatively sliding, them apart. Therefore, the flexible conductive compositions can form reversible electrical connections e.g., for soft, flexible electronics such as biosensors and other bioelectronics. However, permanent connections formed using the flexible conducting compositions are also encompassed.

The MCI from which the flexible conducting compositions are formed also generally includes an adhesion promoter to prevent dried ink (i.e., a flexible conductive composition) from dissolving in water or smudging. In some aspects, the ink also comprises a surfactant. In some aspects, the MCI comprises iron oxide nanoparticles mixed with a conducting polymer in an aqueous (e.g., water) dispersion and is thus water-dispersible and biodegradable. In some aspects, to make a solid flexible conducting composition, the multifunctional conducting ink disclosed herein is dispensed through a thin nozzle to form precise lines and/or nodes (micropatterning) on at least one surface of a substrate, followed by drying or curing to harden and solidify the ink.

Sensors and other bioelectronics produced using the multifunctional conducting ink and/or comprising the solid flexible conducting compositions made therefrom are also encompassed by various embodiments of the invention. In addition, a flexible device made according to the embodiments of this invention may simply be converted to a rigid device by simply placing the device(s) on a rigid backing.

It is an object of the invention to provide an ink, comprising conducting nanoparticles which are nanopolymers, ferromagnetic nanoparticles, an adhesion promoter, an aqueous carrier, and optionally, one or both of a surfactant and a stabilizer, wherein the conductive nanoparticles are separate from the ferromagnetic nanoparticles. That is, it should be understood they are different, separate physical entities, as opposed to a combined single entity; however, in the composition which includes the aqueous carrier they are not necessarily separated from each other, rather they can physically be adjacent to one another, as would occur when an aqueous carrier is dehydrated from an ink which includes several nanoparticles of the two types of different physical entities, just not physically joined into a single physical entity (such as, for example, a coating of a nanopolymer onto a surface of a ferromagnetic nanoparticle). In some aspects, the conducting nanopolymers are PEDOT:PSS (poly(3,4-ethylenedioxythiophene) polystyrene sulfonate), polypyrrole or polyaniline nanopolymers. In some aspects, the ferromagnetic nanoparticles are $Fe_2O_3$ and/or $Fe_3O_4$. In further aspects, the conducting nanopolymers are PEDOT:PSS nanopolymers and the ferromagnetic nanoparticles are $Fe_3O_4$. In additional aspects, the adhesion promoter is a salt of a styrene maleic anhydride copolymer. In some aspects, the surfactant is polysorbate 20. In other aspects, the stabilizer is a polyoxazoline, a poly(glycerol), a polyacrylamide, or a polyethylene glycol. In additional aspects, the ink is magnetic. In yet further aspects, a ratio of the conductive nanoparticles to the ferromagnetic nanoparticles ranges from 1:1 to 1:3.

Also provided herein is a flexible sensor comprising, a sensor, a flexible substrate material that is connected to or part of the sensor, and a flexible, conducting ferromagnetic solid, wherein the flexible, conducting ferromagnetic solid is dehydrated from an ink comprising conducting nanoparticles which are nanopolymers, ferromagnetic nanoparticles, an adhesion promoter and, optionally, one or both of a surfactant and a stabilizer, and wherein the flexible, conducting ferromagnetic solid is reversibly connectable to a magnet. In some aspects, the conducting nanopolymers are PEDOT:PSS (poly(3,4-ethylenedioxythiophene) polystyrene sulfonate), polypyrrole or polyaniline nanopolymers. In other aspects, the ferromagnetic nanoparticles are $Fe_2O_3$ or $Fe_3O_4$ nanoparticles. In additional aspects, the conducting nanopolymers are PEDOT:PSS nanopolymers and the ferromagnetic nanoparticles are $Fe_3O_4$ nanoparticles. In other aspects, the adhesion promoter is an ammonium salt of styrene maleic anhydride. In further aspects, the surfactant is polysorbate 20. In yet further aspects, the stabilizer is a polyoxazoline, a poly(glycerol), a polyacrylamide, or a polyethylene glycol. In other aspects, the flexible device is a biosensor, an antenna or a microsupercapacitor. In some aspects, the flexible substrate is or comprises a flexible adhesive layer. In other aspects, the flexible substrate is formed from or comprises fabric, paper or a polymeric material. In additional aspects, the sensor is magnetic. In yet further aspects, the sensor is a biosensor. In other aspects, a ratio of said conductive nanoparticles to ferromagnetic nanoparticles ranges from 1:1 to 1:3.

Also provided is a bio-sensor, comprising: a sensor configured for attachment to biological tissue; and a ferromagnetic solid which is reversibly, both physically and magnetically, connected to the sensor, wherein the ferromagnetic solid is dehydrated from a conductive ink comprising conductive nanoparticles that are nanopolymers, ferromagnetic nanoparticles, an adhesion promoter, and an aqueous carrier, wherein the conductive nanoparticles are separate from the ferromagnetic nanoparticles, and wherein a ratio of said conductive nanoparticles to ferromagnetic nanoparticles ranges 1:1 to 1:3. In some aspects, the bio-sensor further comprises one or more of a surfactant and a stabilizer. In other aspects, the ferromagnetic particles are $Fe_3O_4$ and the conducting nanoparticles are PEDOT:PSS nanoparticles.

BRIEF DESCRIPTION OF THE DRAWINGS

FIG. 11. Sensor with magnet formed from MCI for attachment to a magnetic connector with wires.

FIG. 12A and B. A) MCI on a substrate; B) I-V curve of the ink showing its low resistance.

FIG. 13A and B. Comparison of electrical properties of ink versions 2.0 and. 4.0 vs. silver paste. A) MCI on a substrate; B) electrical properties of the two versions of the ink.

FIG. 14A-D. Various embodiments compared to prior art. A) conventional magnetic connections; B) exemplary embodiment of a 3-electrode system with connection nodes formed using the MCI; C) exemplary embodiment of a design of a magnetic connector to a achieve physical and electrical connection; D: showing the connection between B and C. The connector is placed on the nodes to achieve a physical and electrical connection.

7                                                          8

Figure 15A:
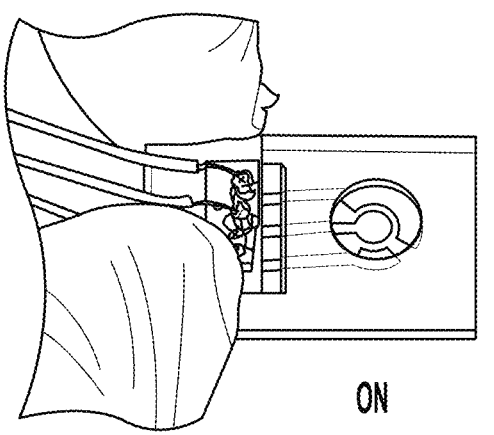
FIG. 15A and B. Use of the MCI to form transient connections. A) connection on; B) connection off.

FIG. 16A and B. A) current response of device of FIG. 15 in ON/OFF states; B) the stability of the current following multiple ON/OFF connections.

FIG. 17A-C. Sensing of uric acid concentration. A) chronoamperometry used for the detection of uric acid in the range of 20-300 μM; B) calibration curve using the MCI connected to the sensor, C) the calibration plot of uric acid sensing with a magnetic connection compared to a conventional silver paste connection.

FIG. 18A and B. Examples of configurations in which a flexible and conformable device is placed on an irregular surface (e.g. tissue) and a connection is made via the magnetic ink deposited on nodes. A) multiplexed electrode with different channels on soft tissue; B) single working electrode on stiffer tissue.

DETAILED DESCRIPTION

Disclosed herein are magnetic inks that are used to form reversible electrical connections between surfaces.

Definitions

An electrical sensor (electronic sensor) is a device that detects a physical parameter of interest (e.g., temperature, pressure, heat, light, sound, etc.) and converts it into electrical signal that can be measured and used by an electrical or electronic system.

Flexible electrical sensors are capable of bending easily without breaking and can be seamlessly applied to soft and irregularly shaped surfaces such as the human skin or textile fabrics.

Conductive polymers (intrinsically conducting polymers, ICPs) are organic polymers that conduct electricity. Such compounds may have metallic conductivity or can be semiconductors.

A nanoparticle, nanopolymer or nano-copolymer has at least one dimension in the range of 1-50 nm.

A ferromagnetic body or substance has a high susceptibility to magnetization, the strength of which depends on that of an applied magnetizing field, and which may persist after removal of the applied field.

A magnet is a material or object that produces a magnetic field. This magnetic field is invisible but is responsible for the most notable property of a magnet: a force that pulls on ferromagnetic materials, such as iron, steel, nickel, cobalt, etc. and attracts or repels other magnets.

A permanent magnet is an object made from a material that is magnetized and creates its own persistent magnetic field. Materials that can be magnetized, which are also the ones that are strongly attracted to a magnet, are called ferromagnetic (or ferrimagnetic). These include the elements iron, nickel and cobalt and their alloys, some alloys of rare-earth metals, and some naturally occurring minerals such as lodestone.

Composition of the Multifunctional Conductive Ink (MCI)

The multifunctional conductive ink disclosed herein comprises i) electrically conductive nanopolymers and ii) ferromagnetic and/or magnetic nanoparticles. The electrically conductive nanopolymers and the ferromagnetic and/or magnetic nanoparticles are suspended in an aqueous liquid carrier as separate particles, i.e., they are not combined in a single particle having a core-shell structure. In other words, they are not layered and the properties of ferromagnetism and/or magnetism and electrical conductivity are not both present in a single nanoparticle. Instead, the ink comprises a mixture of at least two separate types of nanoparticles, one of which is ferromagnetic and/or magnetic, and one of which is an electrically conductive nanopolymer. In other words, the conductive nanoparticles are separate from the ferromagnetic nanoparticles. It is noted that the ferromagnetic nanoparticles may or may not be intrinsically magnetic.

With respect to conducting nanopolymers, any conducting nanopolymer capable of forming a water dispersion may be utilized. Conducting nanopolymers that cannot form a water dispersion are generally excluded.

Examples of conducting nanopolymers that are used include but are not limited to: poly(fluorene)s, polyphenylenes, polypyrenes, polyazulenes, polynaphthalenes, poly (pyrrole)s (PPY), polycarbazoles, polyindole, polyazepines, polyanilines (PANI), poly(thiophene)s (PT), poly(3,4-ethylenedioxythiophene) (PEDOT), poly(acetylene)s (PAC), poly (p-phenylene vinylene) (PPV), etc. and combinations (nanocomposites) of these such as poly(3,4-ethylenedioxythiophene) polystyrene sulfonate (PEDOT:PSS); etc.

Any form of ferromagnetic and/or magnetic nanoparticle for which a water suspension can be made may be used to form the MCI, including those currently being developed such as e.g., carbon coated metallic particles. Further examples of ferromagnetic and/or magnetic nanoparticles that are used include but are not limited to: iron oxide ($Fe_3O_4$ and/or $Fe_2O_3$ nanoparticles) and magnetic iron oxide ($Fe_3O_4$ and/or $Fe_2O_3$ nanoparticles), superparamagnetic iron oxide nanoparticles (SPIONs), Co, Ni, alloys, rare earth metals etc.

The amount of each of these two principal components is generally in the range of, for the conducting polymer: from about 2 to about 50 mg/ml of ink, such as from about 3 to about 40, or from about 4 to about 30 and is typically from about 5 to about 20 mg/ml, i.e. about 5, 6, 7, 8, 9, 10, 11, 12, 13, 14, 15, 16, 17, 18, 19, or 20 mg/ml of ink. For the ferromagnetic/magnetic nanoparticles, the amount is from about 1 to about 25, or about 2.5 to about 20, or from about 5 to about 15 mg/ml, i.e., about 5, 6, 7, 8, 9, 10, 11, 12, 13, 14, or 15 mg/ml or ink. Typically, the mount of conducting polymer is from about 5 to about 20 mg/ml and the amount of magnetic component is from about 5 to about 15 mg/ml.

The ratio of conducting polymer to ferromagnetic/magnetic component is generally from about 1:1 to about 3:2, e.g., about 1.5:1, 2.0:1.0, 2.0:1.5, 2.5:1.0, 2.5:1.5, 2.5:2.0. 3.0:1.0, 3.0:1.5, etc. including all decimal fractions in between.

The conducting polymers and the magnetic component are generally dispersed or suspended in a carrier, typically an aqueous carrier such as water, because it is a "green" solvent.

In some aspects, one or more surfactants is also present in the ink. Examples of suitable types include surfactants include but are not limited to various known anionic, cationic, Zwitterionic and non-ionic surfactants. Surfactants which are nonionic, anionic (i.e., soaps, sulfonates), cationic (i.e., CTAB), zwitterionic, polymeric or amphoteric may be used. Exemplary surfactants include but are not limited to: acetylene glycol-based surfactants, polyoxyethylene alkyl ether-based surfactants, polyoxyethylene alkylphenyl ether-based surfactants, fluorine-based surfactants (fluorosurfactant, e.g., as taught in issued U.S. Pat. Nos. 8,752,948 and 9,957,401, the complete contents of each of which is hereby incorporated by reference in entirety), silicone-based surfactants, polysorbate-type nonionic surfactant, etc.

Other exemplary surfactants are taught e.g., in issued U.S. Pat. Nos. 8,651,650; 8,435,339; and 10,907,064, the complete contents of each of which is hereby incorporated by reference in entirety.

In some aspects, the surfactant is a non-ionic surfactant. Examples of suitable nonionic surfactants include, linear or secondary alcohol ethoxylates (such as the Tergitol® 15-S and Tergitol® TMN series available from Dow Chemical Company and the Brij® series from Croda International Plc.), ethoxylated alkyl phenols (such as the Triton® series from Dow Chemical Company), fluoro surfactants (such as the Zonyls® from DuPont; and the Fluorads® from 3M), fatty acid ethoxylates, fatty amide ethoxylates, ethoxylated and propoxylated block copolymers (such as the Pluronic® and Tetronic® series from BASF Corp., ethoxylated and propoxylated silicone based surfactants (such as the Silwet® series from Momentive), alkyl polyglycosides (such as the Glucopons from Cognis GmbH since acquired by BASF Corp.) and acetylenic diol polyethylene oxide surfactants (such as the Surfynol® family from Air Products and Chemicals Inc.). Additionally, any conformationally asymmetric water-soluble polyoxygenated hydrocarbons enabling surface tension reduction can be employed as a surfactant.

In some aspects, the surfactant is a polysorbate-type nonionic surfactant. Exemplary non-ionic surfactants include e.g. fatty acid esters of sorbitol, examples of which include but are not limited to: Polysorbate 20 [(polyoxyethylene (20) sorbitan monolaurate], common commercial brand names of which include Kolliphor PS 20, Scattics, Alkest TW 20, Tween® 20, and Kotilen-20); Polysorbate 40 [Polysorbate 40 (polyoxyethylene (20) sorbitan monopalmitate)]; Polysorbate 60 [(polyoxyethylene (20) sorbitan monostearate)] and Polysorbate 80 [(polyoxyethylene (20) sorbitan monooleate].

In some aspects, the surfactant is Polysorbate 20.

In addition, the MCI composition generally includes at least one stabilizer, i.e., a substance which make it possible to maintain the physico-chemical state of a homogenous dispersion of two or more immiscible substances. Examples of categories of suitable stabilizers include but are not limited to: Polyoxazolines (POX/POZ), Poly(N-vinylpyrrolidone) (PVP), Poly(glycerols) (PG), Polyacrylamides, Poly(N-(2-hydroxypropyl)methacrylamide) (pHPMA), etc.

In some aspects, the stabilizer is a hydrophilic stabilizer. Examples of hydrophilic stabilizers include but are not limited to: polyethylene glycol (PEG) stabilizers, such as PEG 400, glycerol, poly(glycerols), poly(N-(2-hydroxypropyl)methacrylamide) (pHPMA), etc.

In addition, the MCI compositions generally include at least one adhesion promoter. Adhesion promoters are generally used to ensure that the ink, upon drying, is impermeable to water and thus will not run or smudge. Examples of adhesion promoters include but are not limited to those described in issued U.S. Pat. No. 3,991,032, the complete content of which is hereby incorporated by reference in entirety. Examples include the ammonium salts of olefin/maleic anhydride copolymers or polyolefin/maleic anhydride copolymers. In some aspects, the adhesion promoter is an ammonium salt of styrene maleic anhydride.

Other components that may be included in the liquid ink include but are not limited to, for example: various colorants, pigments and/or dyes; fluorescent dye; curing agents such as photo initiators, photopolymers or light activated resins (e.g., azobisisobutyronitrile, 2,2-Dimethoxy-2-phenylacetophenone, wetting agents, so-called humectants, biocides, dispersing agents, binding agents, anti-foam agents, and pH control agents including pH buffer agents, etc.

Exemplary MCI Compositions

In some exemplary aspects, the MCI that is disclosed herein comprises at least one type of electrically conductive nanopolymer and at least one type of ferromagnetic nanoparticle in an aqueous suspension. An example is denominated herein in the Examples section as version 2.0. MCI 2.0 does not contain any stabilizer or adhesion promoter. In other exemplary aspects, denominated herein in the Examples section as version 4.0, the MCI also comprises at least one surfactant and at least one adhesion promoter.

These exemplary aspects are not limiting and many other formulations of the MCI are also encompassed. For example, the MCI may comprise one or more than one type of electrically conductive nanopolymer; and/or one or more than one type of ferromagnetic nanoparticle; and/or one or more than one type of adhesion promoter, and/or one or more than one type of stabilizer. "One or more than one" may be indicated hereby by reciting "at least one".

Exemplary Devices

A unique property of this water dispersible ink is that it can be used to form a flexible conductive ferromagnet or magnet that can form connections that are both physical (e.g., via magnetic attraction) and electrical.

Figure 1A:
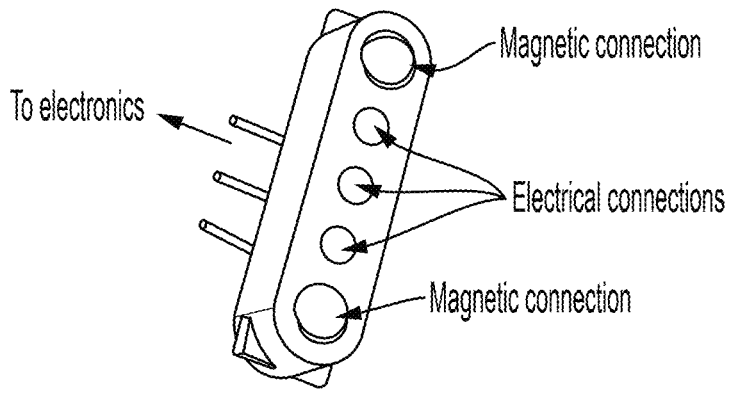
FIG. 1A-C. A, Typical prior art magnetic connector; B, schematic representation of an exemplary embodiment of a flexible device made with the magnetic, electrically conductive ink disclosed herein; C, the water-based ink may be extruded using a fine nozzle or syringe needle to form of patterns or nodes.
Figure 1B:
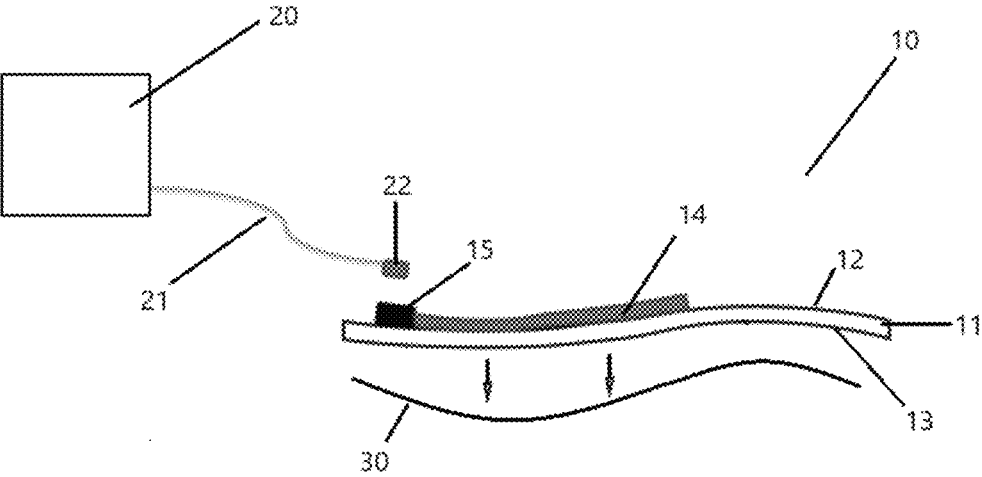

The FIG. 1B shows an exemplary flexible device made using the MCI disclosed herein. What is shown is flexible device 10 comprising flexible substrate 11 having first surface 12 and second surface 13. Sensor/electrode 14 (which may be a patterned sensor/electrode) is attached or adhered directly to first surface 12. In some aspects, first surface 12 may also comprise a topcoat to foster good adhesion of the MCI (not shown).

In some aspects, sensor/electrode 14 is patterned or printed using the MCI, which is typically water-based and thus biodegradable. In other aspects, sensor/electrode 14 is made from a different conducting material. In some aspects, sensor/electrode 14 is a microelectrode and may function as a biosensor, antenna, a microsupercapacitor for energy storage, actuators, transistors, neural prosthetics, etc.

Flexible conducting ferromagnet 15 is formed by deposition of the MCI disclosed herein onto first surface 12 and thus is also attached directly to first surface 12. Flexible conducting ferromagnet 15 is attached directly to first surface 12 immediately adjacent to and abutting/touching/contiguous with sensor/electrode 12 so as to be electrically connected to sensor/electrode 12, i.e., an electrical current can pass between them freely. In some aspects, the multifunctional ink is used to form nodes on sensor/electrode 14 so as to permit coupling of flexible device 10 with device 20 as described below.

Also shown is device 20 comprising magnet 22, which may be a permanent magnet and may or may not be flexible. Magnet 22 is generally a conductive magnet. In some aspects, magnet 22 is a strong Nd magnet. Similarly, a copper wire soldered to a microscale Nd magnet may be used. In some aspects, device 20 is a conventional device (which may be rigid) such as: a power source; a connector that connects to a source of electricity (e.g., a "charger" such as a charger for a laptop, cell phone, etc. that plugs into a wall outlet); a single or multi-channel potentiostat; a data telemeter; source meter, voltmeter, hand-held reader; etc. In some aspects, connector 21 is optionally present to connect magnet 22 to device 20. For example, connector 21 may be an electrical cord.

Magnet 22 thus allows or is used to establish a physical connection between device 20 and the electronics of flexible device 10. No tape or adhesive is used to form the connections; the electrical connection is achieved by magnetic attraction alone. Flexible conducting ferromagnet 15 allows or is used to establish electrical connections for two-way communication from and to (between) device 20, which may be a rigid device, and flexible device 10.

In some aspects, flexible substrate 11 is a material such as cloth, fabric, silk protein, paper, textile, etc. In such aspects, the cloth or fabric may be part of a garment, such as a wearable garment. Alternatively, flexible substrate 11 is a material such as a polymeric material or plastic and (optionally) forms part of a wearable garment or other wearable article, e.g., a watch band, fit bit, etc. In these aspects, flexible conducting ferromagnet 15 is, in effect, formed directly on the article (flexible substrate 11 is part of or a section of the article).

In other aspects, flexible conducting ferromagnet 15 is formed on flexible substrate 11 and flexible substrate 11 is attached to another different substrate, shown in FIG. 1B as substrate 30. The attachment may be e.g., via second surface 13 of flexible substrate 11. Second surface 13 may comprise or be an adhesive/adhesive surface in order to adhere to substrate 30, or may be connectable to substrate 30 by another means, e.g., sewing, via a Velcro connection, by snaps, via a zipper, etc.

In some aspects, for example, when flexible device 10 is part of a biosensor, substrate 30 may be skin, such as human skin. In this aspect, second surface 13 generally comprises an adhesive which allows temporary attachment to and later removal from the skin. Use as a biosensor implies that the connection is temporary (as long as the magnet is in contact with the dried, solidified ink on the sensor, it is possible to get a reading. When the magnet is removed, the connection is lost).

Making Flexible Conductive Ferromagnetic Connects

Figure 1C:
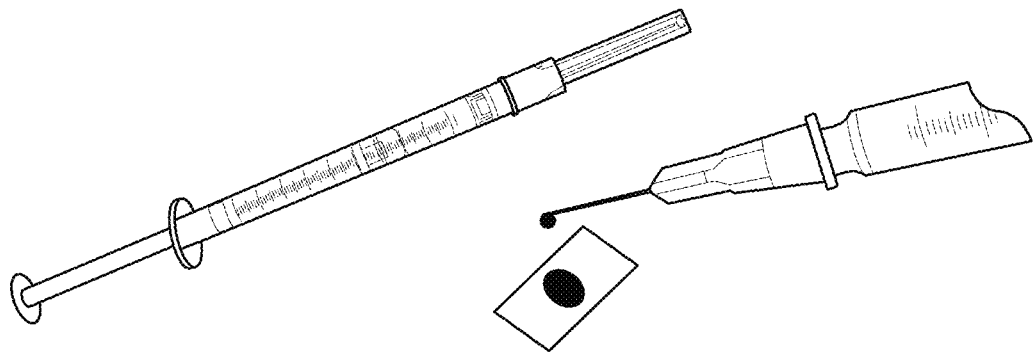
Figure 2A:
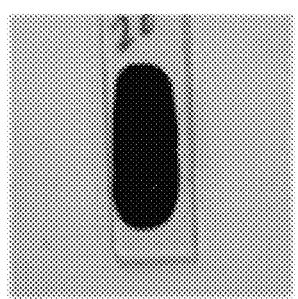
FIG. 2A-D. A) A sample 20% $Fe_3O_4$ in PEDOT:PSS/PS composite on a glass slide, B) electrical connections made to a 10% $Fe_3O_4$ in PEDOT:PSS/PS composite, C) magnet brought near pure $Fe_3O_4$ liquid shows the liquid being pulled towards the magnet and D) I-V scans performed on 5, 10 and 20% composites.
Figure 2B:
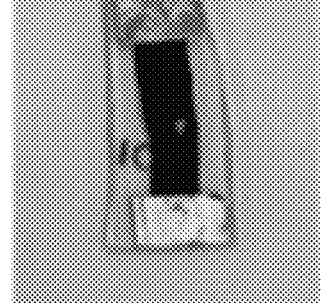
Figure 2C:
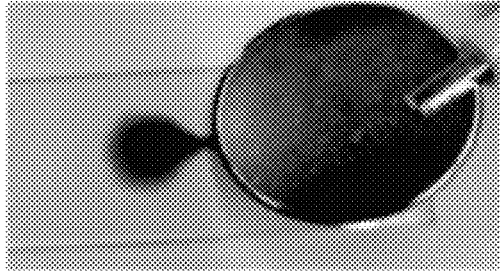
Figure 2D:
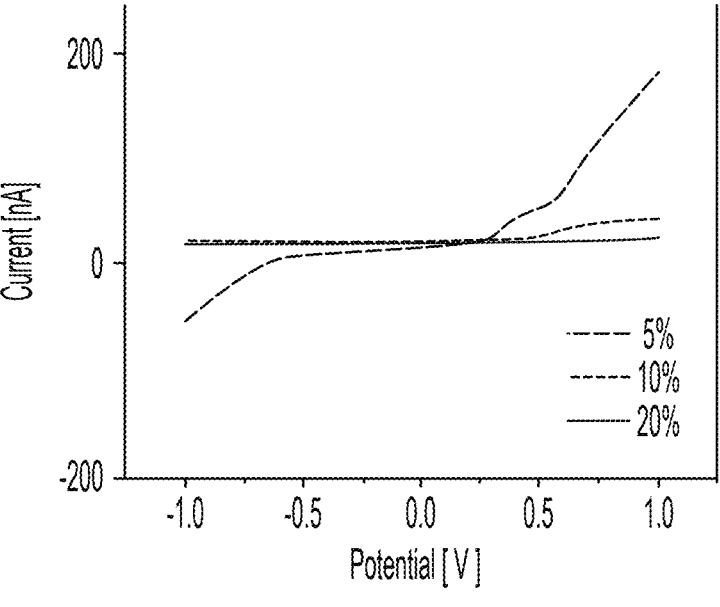

Methods of making the flexible conductive ferromagnetic connects are also encompassed. Generally, the flexible conductive ferromagnetic connects disclosed herein are made by dispensing, onto a substrate, the MCI disclosed herein using e.g., a fine nozzle having a suitable diameter and capable of a suitable flow rate. The ink is of a consistency so as to be amenable to dispensing even by e.g., a syringe (see FIG. 1C). In other aspects, the MCI is sprayed onto a substrate.

Examples of nozzles and the machines which employ them e.g., for printing magnetic or other patterns on substrates include those described in issued U.S. Pat. No. 8,096,263B2 and published US patent application 20190333695, the complete contents of both of which are herein incorporated by reference in entirety.

For manufacturing, the MCI may be provided to a user i) in a reconstitutable dry particulate form or ii) in a concentrated liquid form that is diluted by the user prior to use or iii) in a ready to use liquid form. If provided in a dry or dilutable form, the printing machines may comprise an ink mixer that receives i) the dry form and adds a suitable aqueous medium, or ii) receives the concentrated liquid form and dilutes it with a suitable aqueous medium. Once at the final desired concentration, the ink mixer can operate continuously or intermittently to produce MCI that flows intermittently or continuously to an ink supply from which the ink is dispensed. The intermittent or continuous flow of MCI may be used e.g., in a manufacturing facility, for example, on an assembly line, where a plurality of flexible magnets are produced as an intermittently or continuously running manufacturing process.

In some aspects, the machine comprises an ink pump to receive MCI from the ink supply and discharge the MCI at a controlled pressure. In some aspects, particularly in a manufacturing facility, such as on an assembly line, the ink pump may be a continuously operating pump that provides a continuous flow of MCI to a nozzle for dispensing. The machine typically comprises a nozzle and e.g., a stationary or moveable platform, such as an x-y movable platform. The ink pump is fluidly connected to the nozzle to deliver magnetic conductive ink to the nozzle, and the nozzle produces (ejects, dispenses, expels, etc.) an ink filament when the magnetic ink is forced therethrough under pressure by the ink pump. The dispensed ink filament attaches to a substrate (e.g., a flexible substrate) which may be held in position on the platform. In some aspects, a predetermined pattern is formed by the ink extruded onto the platform by the movement of the platform. Alternatively, the platform holding the substrate may be stationary and the nozzle may be moveable over the substrate to deposit the ink onto the substrate in the desired pattern.

In some aspects, a single extrusion and printing of ink takes place so that a single layer of ink is deposited and then cured or dried. In other aspects, multiple layers of ink are deposited, generally after a preceding layer is cured or dried, and a multi-layer conductive magnetic pattern is formed.

Devices and Systems

Embodiments of the invention are is related to the use of the MCI ink and flexible ferromagnets formed from the ink described herein. Possible uses of the technology include but are not limited to: flexible sensors, biosensors, antennae, energy storage devices (e.g., made from soft and/or biodegradable materials such as thin biomaterial films, paper or textiles). This technology has applications in wearable technologies (e.g., on skin or smart textiles), either for medical purposes (such as biosensors) or as fashion accessories, or for any other purpose. Accordingly, the present disclosure also provides such devices and systems comprising the devices, as illustrated schematically in FIG. 1B.

Moreover, it will be recognized that the flexible devices made according to the embodiments of this invention may simply be converted to rigid devices by simply placing them on a rigid backing.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLES

Various trials were conducted to optimize the multifunctional ink disclosed herein and to demonstrate that magnetic connectors may be attached to a sensor with magnetic connection ink in order to obtain readings (electrical signals) without the use of any other connection.

Materials

A water dispersion of PEDOT:PSS was obtained from Sigma Aldrich (St. Louis, MO). A water dispersion of $Fe_3O_4$ nanoparticles is obtained from US Research Nanomaterials Inc. (Houston, TX). PEDOT:PSS is readily commercially available.

EXAMPLE 1. Trial Using Dry Pellets

A dispersion of 1% (w/v) PEDOT:PSS in water was made. 100 mg of PEDOT:PSS dry pellets (Sigma Aldrich) was added to 10 ml water and sonicated for 15 mins. The mixture was ultrasonicated for 1 hr. in an ice bath. Photocrosslinkable silk sericin (PS) protein was used as a carrier. Using the PEDOT:PSS dispersion in water, a 28% (w/w) PEDOT:PSS/PS was made. ~28% (w/w) composite was obtained by mixing 40 μL of PEDOT:PSS per mg of PS. A 20 wt. % dispersion of $Fe_3O_4$ in water was obtained from US Research Nanomaterials. $Fe_3O_4$ dispersion in water was added to the PEDOT:PSS/PS composite to obtain a 5% (w/w) of $Fe_3O_4$ in PEDOT:PSS/PS. This was achieved by adding 0.4 μL 20 wt. % $Fe_3O_4$ dispersion in water to 40 μL PEDOT:PSS/PS composite. Similarly, ink composites with the 10 and 20% (w/w) $Fe_3O_4$ was also made. 40 μL of each ink composites with 5, 10 and 20% $Fe_3O_4$ was casted on to clean glass slides, dried under ambient conditions and crosslinked under UV light for 3 seconds in order to test their magnetic behavior and electrical conductivity. Electrical connections were made by applying silver paste on each end of the film and pasting copper tape on it.

Results:

None of the composites showed magnetic behavior near a magnet. The composite liquids were cast onto clean glass slides and a magnet was brought near to the liquid. The liquids did not flow towards the magnet. However, when pure 20% $Fe_3O_4$ liquid was brought close to a magnet, the liquid was visibly attracted towards the magnet. I-V scans were performed on the composites in the range of –1V to 1V did not reveal any significant electrical conductivity. The 5% composite gave the highest current reading of ~160 nA at 1V potential. The 20% composite did not show any conductivity. It can be deduced that increasing the concentration of $Fe_3O_4$ in the composite resulted in the decrease of conductivity. However, even at 5% concentration, the current was not sufficient to make electrical connections. See FIG. 2A-D.

EXAMPLE 2. Trial Using Commercial Ferrofluid

A commercially available ferrofluid was used to make a conductive magnetic composite by mixing it with PEDOT:PSS/PS composite. 1% (w/v) dispersion of PEDOT:PSS was used to make a 28% PEDOT:PSS/PS composite. Ferrofluid was added to the 28% PEDOT:PSS/PS composite in amounts of 10% and 20% (v/v). The mixture was vortexed for 1 hour. The prepared ferrofluid/PEDOT:PSS/PS composite was cast on a clean glass slide and dried at 600° C. until all the solvent evaporated. The samples were then exposed to UV light for 3 seconds. The magnetic behavior of the composites was tested by bringing a neodymium magnet close to the composites (on glass slides) and monitoring for any signs of attraction towards the magnet. Electrical conductivity was tested by performing I-V scans on the composites. Electrical connections were made using silver paste and copper tape.

Results:

The ferrofluid was difficult to work with as it stained everything it came in contact with. The ferrofluid/PEDOT:PSS/PS composites did not exhibit magnetic behavior when a magnet was brought in close contact. However, when pure ferrofluid was cast on a clean glass slide, dried in an oven and brought close to a magnet, a weak attraction between the composite and the magnet was observed. When I-V scans were performed on the composites, including pure ferrofluid on a glass slide, in the range of –1V to 1V at a scan rate of 100 mV/sec, none of the composites showed any conductivity (data not shown). Only noise was recorded. It was deduced that ferrofluid was not suitable for making electrical connections as it did not show any electrical conductivity.

EXAMPLE 3. Magnetic Composites on Photocrosslinked Silk Fibroin (PSF) Films

To test the magnetic behavior of magnetic composites on flexible, photocrosslinked silk fibroin (PSF) biomaterial films, ferrofluid was deposited. The PS film was made by dissolving photocrosslinkable silk fibroin protein in formic acid (FA) (7.5% w/v) and adding 2.5% (w/v) photo initiator to the composite. The PSF/FA solution was cast onto clean glass slides, dried under the hood until the FA evaporated and exposed under UV light for 3 seconds. 30 μL of ferrofluid was cast onto a 1 cm×1 cm PSF film. The ferrofluid was dried on the PSF film for ~24 hrs. The PSF film with ferrofluid layer on it was peeled off from the glass slide carefully to obtain a free-standing film. The magnetic behavior of the film was tested by bringing a magnet close to it.

Result:

Without heating, the ferrofluid took a long time to dry on the PSF film. The ferrofluid made the PSF film brittle. However, when a magnet was brought close to the film, it attached to the magnet instantly. (Data not shown.)

EXAMPLE 4. Composite of $Fe_3O_4$ and Poly(3,4-Ethylenedioxythiophene) Polystyrene Sulfonate (PEDOT:PSS)

A composite of $Fe_3O_4$ and PEDOT:PSS was prepared following a protocol reported by [2]. 1% (w/v) dispersion of PEDOT:PSS in water was prepared. 10 mg of $Fe_3O_4$ was mixed with 10 ml of PEDOT:PSS and ultrasonicated for 1 hr. The composite was cast onto a clean glass slide and dried in an oven at 100° C. for 1 hr. The film was then carefully peeled off from the glass slide. The magnetic behavior of the film was tested by bringing a magnet near the film. The electrical conductivity of the film was tested by performing an I-V scan on the film from –1V to 1V at a scan rate of 100 mV/sec. The connections were made using silver paste and copper tape.

Figure 3A:
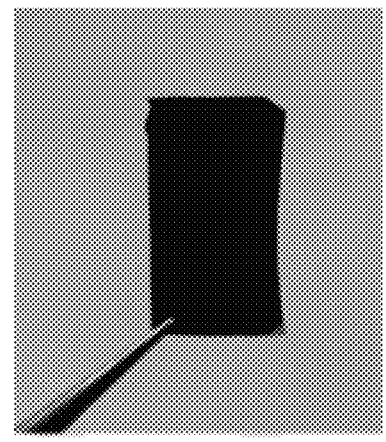
FIG. 3A-C. A) $Fe_3O_4$/PEDOT:PSS film B) a magnet brought near a $Fe_3O_4$/PEDOT:PSS film showing no attraction between them and C) I-V scan performed on the $Fe_3O_4$/PEDOT:PSS film.
Figure 3B:
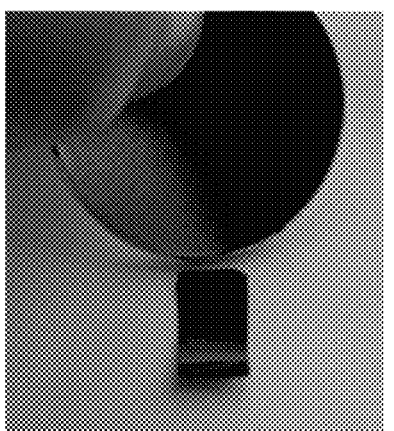
Figure 3C:
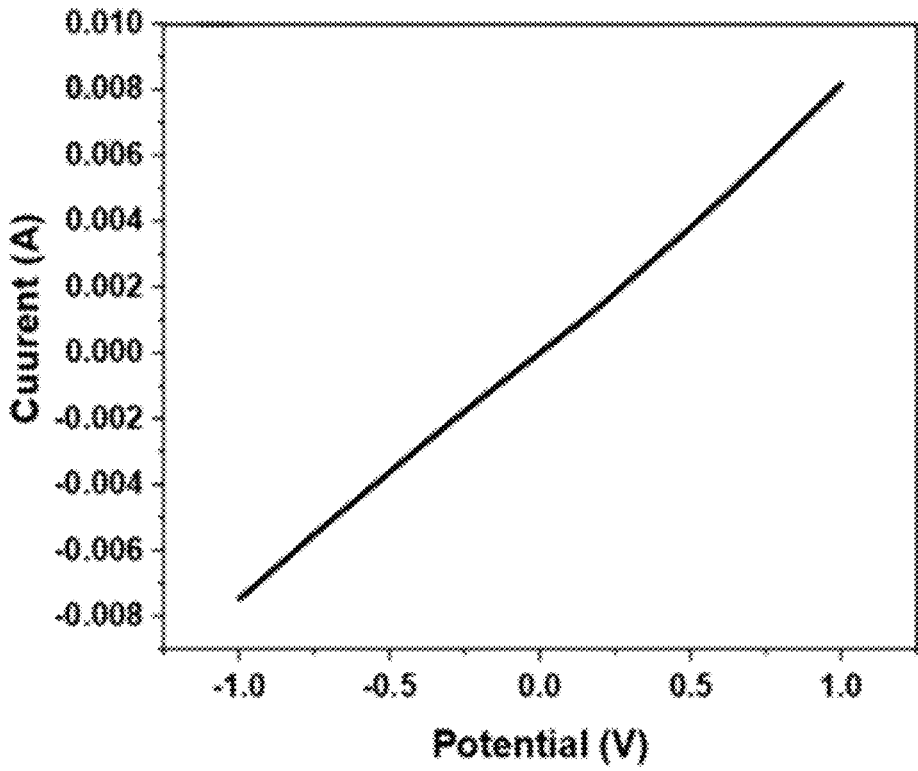

Results:

The $Fe_3O_4$/PEDOT:PSS film did not show magnetic behavior in the presence of a magnet. However, I-V scan performed on the $Fe_3O_4$/PEDOT:PSS film showed a high current value of ~8 mA at 1V potential. Therefore, the 10 mg $Fe_3O_4$/PEDOT:PSS composite is very conductive but does not show magnetic behavior. See FIG. 3A-C.

EXAMPLE 5

Plain $Fe_3O_4$ (20 wt. % in water, US Research Nanomaterials) was cast on a photocrosslinkable silk fibroin (PSF) biomaterial film. The PSF film was prepared using the method described in Example 3. The $Fe_3O_4$ was cast and dried on the silk fibroin film under ambient conditions. The magnetic and electrical properties of the $Fe_3O_4$/PSF film were tested using methods reported in previous Examples.

Figure 4A:
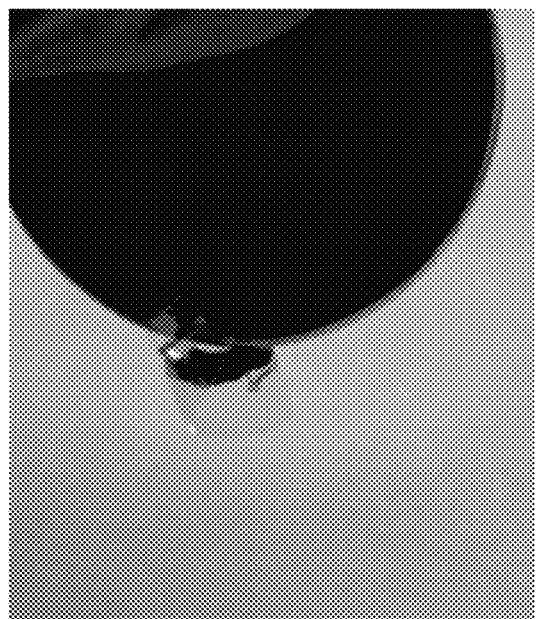
FIG. 4A and B. A) A magnet brought near a $Fe_3O_4$/PSF film shows the film attached to the magnet and B) I-V scan performed on $Fe_3O_4$.
Figure 4B:
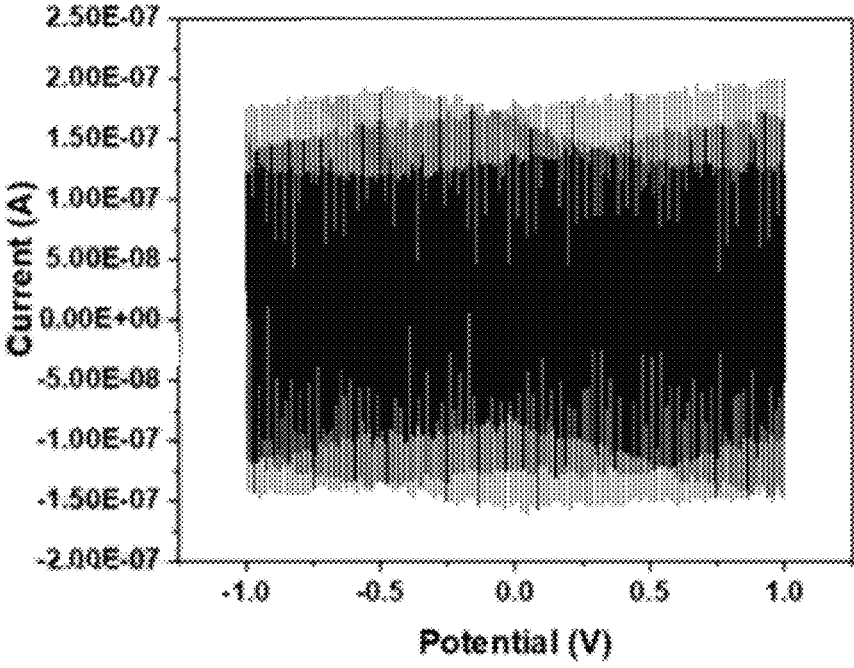

Results:

The $Fe_3O_4$ did not make the silk fibroin (PSF) film brittle. When a magnet was brought close to the $Fe_3O_4$/PSF film, the film instantly attached to the magnet showing good magnetic properties. However, I-V scan performed on $Fe_3O_4$ from –1V to 1V at a scan rate of 100 mV/sec did not show any conductivity and only noise was recorded. $Fe_3O_4$ by itself is thus magnetic but non-conducting. See FIG. 4A and B.

EXAMPLE 6

A composite of $Fe_3O_4$ and PEDOT:PSS was prepared using a similar protocol as that described in Example 4. However, the concentration of $Fe_3O_4$ was increased 3×. 30 mg of $Fe_3O_4$ was introduced into 10 ml 1% (w/v) PEDOT:PSS dispersion by adding 150 μL of $Fe_3O_4$ liquid (20 wt. % in water, US Research Nanomaterials) and ultrasonicated for 1 hr. Following this, the composite was cast on clean glass slides and dried in an oven at 100° C. for 1 hr. The film was then carefully peeled off from the glass slide. The magnetic and electrical properties of the 30 mg $Fe_3O_4$/PEDOT:PSS film was tested using methods reported in previous Examples.

Figure 5A:
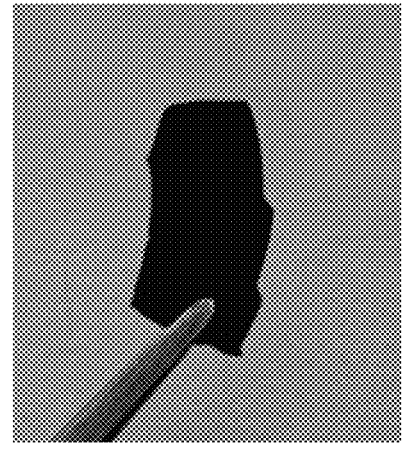
FIG. 5A-C. A) 30 mg $Fe_3O_4$/10 ml PEDOT:PSS film; B) a magnet near a $Fe_3O_4$ PEDOT:PSS film shows the film attracted to the magnet; and C) I-V scan on the $Fe_3O_4$/PEDOT:PSS film.
Figure 5B:
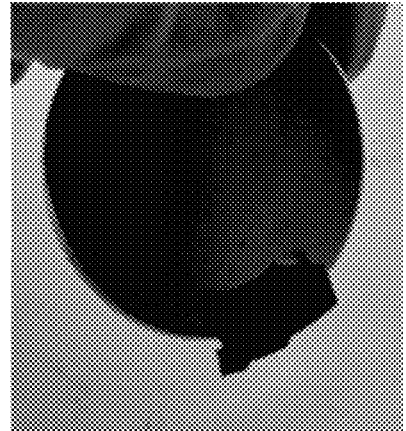
Figure 5C:
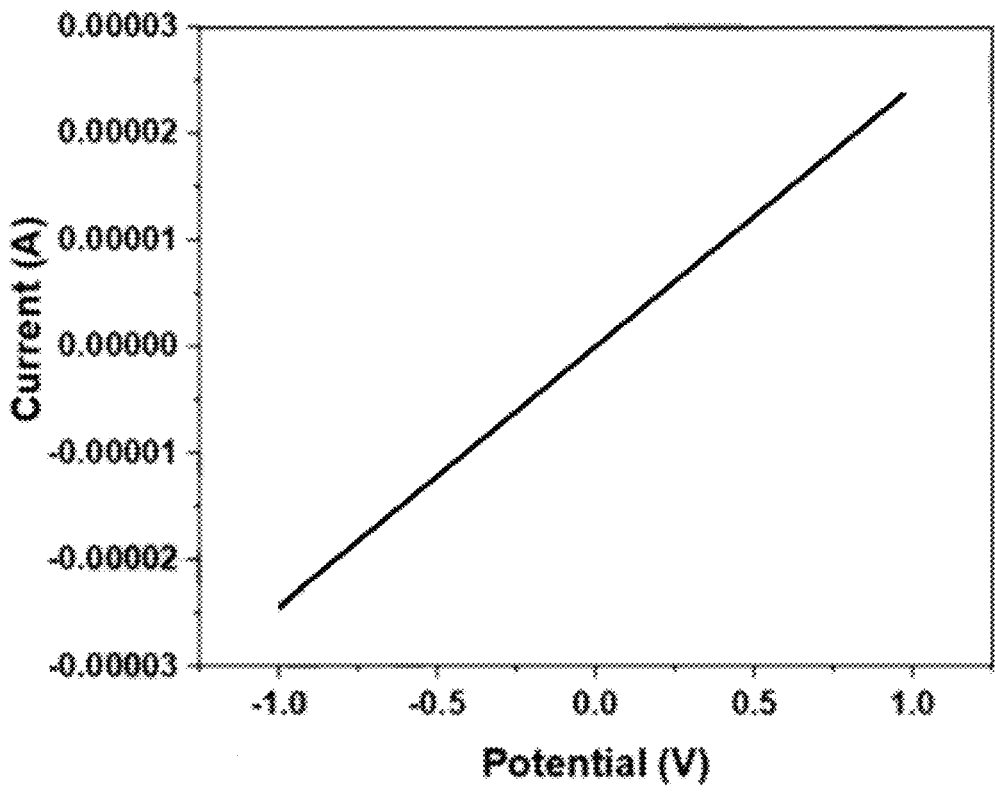

Results:

The 30 mg $Fe_3O_4$/10 ml PEDOT:PSS film attaches to a magnet instantly. I-V scan performed on the $Fe_3O_4$/PEDOT:PSS film showed a moderate current value of ~25 μA at 1V. The conductivity of 30 mg $Fe_3O_4$/PEDOT:PSS composite is low but the composite shows magnetic behavior. Even though the conductivity of the composite is low, it is sufficient to make an electrical connection. See FIG. 5A-C.

EXAMPLE 7

30 μL of PEDOT:PSS/PS ink (28%) was cast on a 2 cm×0.5 cm photocrosslinkable silk fibroin (PSF) film, dried under ambient condition and crosslinked using 365 nm UV light for 3 seconds to form a working electrode on a thin silk film. The PEDOT:PSS/PS electrode was insulated using non-conductive PTFE tape while leaving a 0.79 cm² area exposed which was the electrode. 40 μl magnetic ink (3 mg $Fe_3O_4$/ml PEDOT:PSS) was cast on the electrode and dried in order to make the electrical connections. I-V scans were performed on the sensor by making 3 different connection types to the same sensor: 1. Alligator clip clipped on the magnetic ink, 2. Magnetic ink attached directly to a magnet (desired connection type) and 3. Magnetic ink attached to a magnet using tape. A linear sweep voltammetry scan (LSV) was performed using a 3-electrode setup with Pt wire as the counter electrode and Ag/AgCl as the reference electrode in a potential range of –1V to 1V. 1× PBS, pH 7.4 was used as the electrolyte.

Figure 6A:
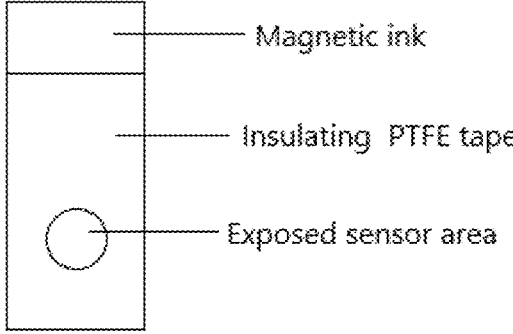
FIG. 6A-C. A) Representation of setup; B) different types of connections made to the electrode; and C) I-V scan performed on the electrode using different connections.
Figure 6B:
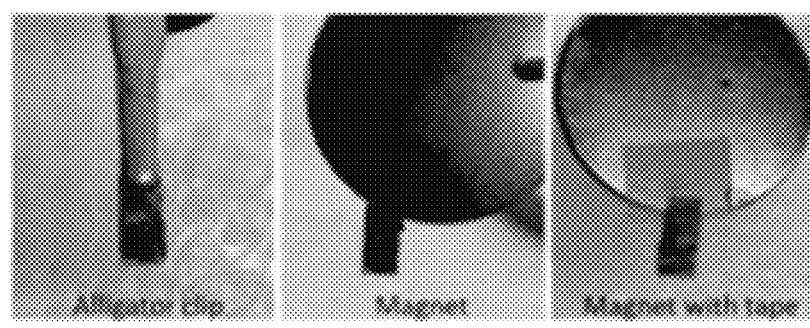
Figure 6C:
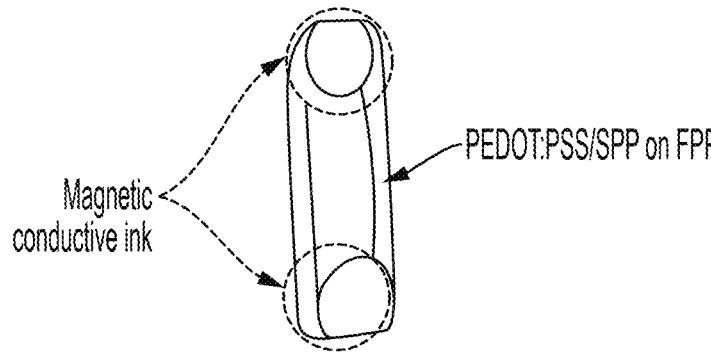
Figure 7A:
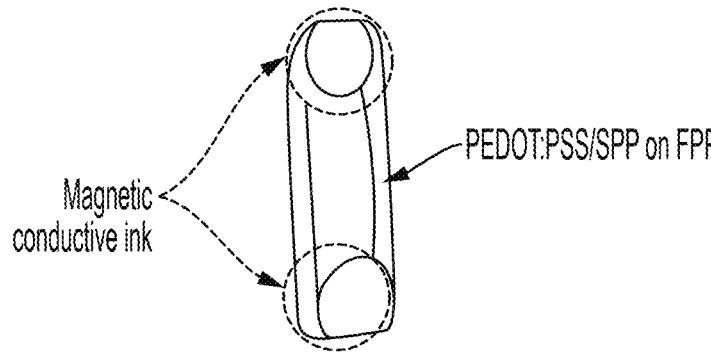
FIG. 7A-D. A) PEDOT:PSS/PS on PSF film with magnetic ink on each end for electrical Connections; B) Temperature sensor on a hot plate; D) I-V curves performed from 20-500° C.; and D) Effect of temperature on the resistance of the PEDOT:PSS/PS on PSF temperature sensor (R0=200 C, n=3).
Figure 7B:
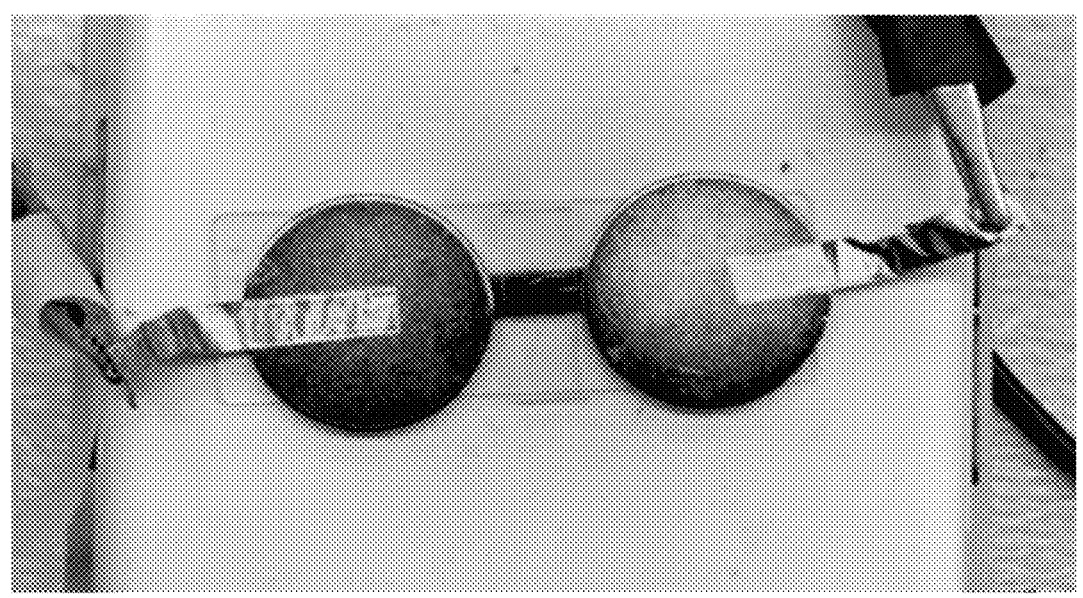
Figure 7C:
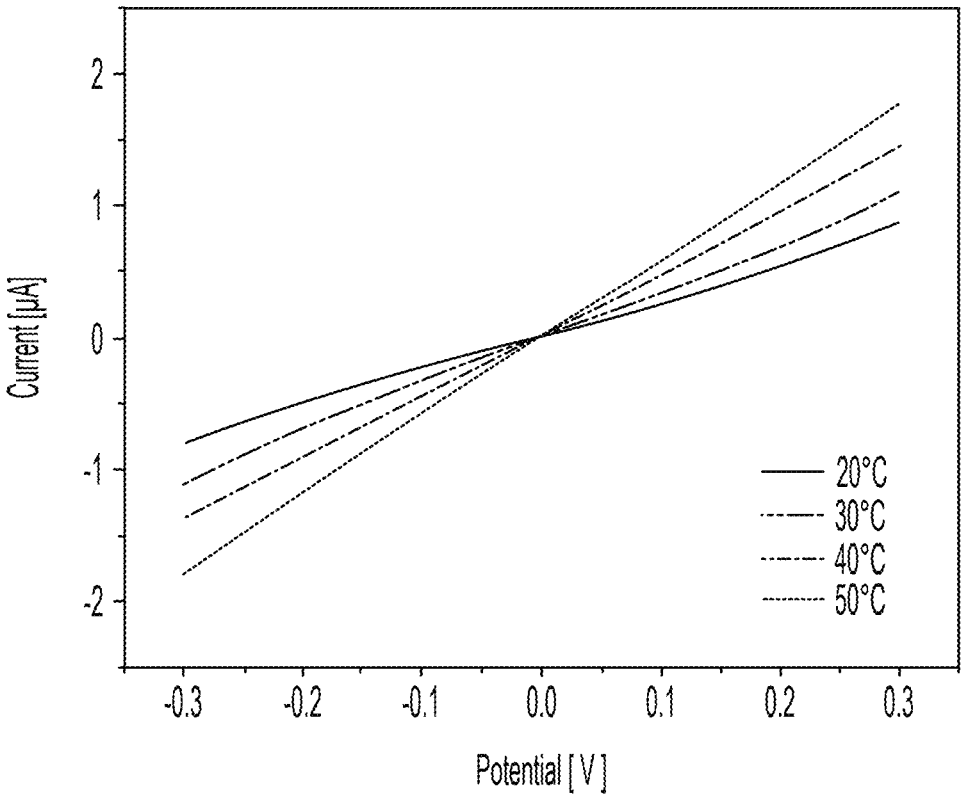
Figure 7D:
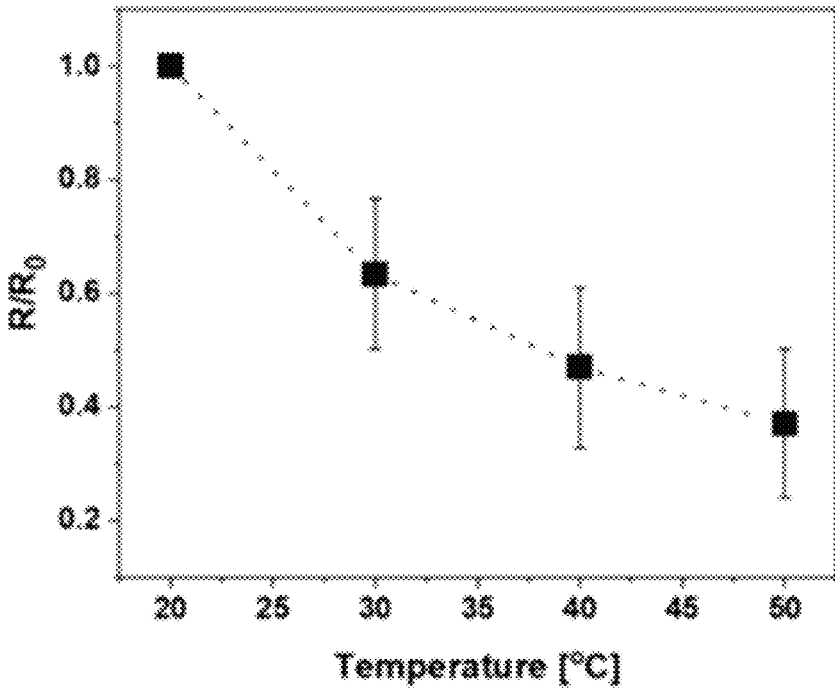

Results:

The electrode was able to give a reading using all 3 connection types. Even though using just the magnet to make connections gave a very low current value at 1V, it is sufficient to be used as a method to make an electrical connection to a sensor. See FIG. 6A-C.

EXAMPLE 8

A PEDOT:PSS/PS electrode on photocrosslinkable silk fibroin (PSF) film was used to determine the effect of temperature on its resistance. In order to make the connections, 40 μL of magnetic ink (3 mg $Fe_3O_4$/ml PEDOT:PSS) was cast on each end of the PEDOT:PSS/PS on PSF film and air dried. The sensor was placed on a hot plate and connections were made using 2 magnets. Copper tape was used on the magnets to extend the connection. I-V scans were performed in the range of –0.3V to 0.3V at 10° C. increments from 20° C. to 50° C. The temperature of the hotplate was confirmed using a commercial IR thermometer.

Results:

The magnetic ink made stable connections to sensors for monitoring any physical parameter. See FIG. 7A-D.

A mixture of 3 mg $Fe_3O_4$/ml PEDOT:PSS (28% in water) was found to have the optimal properties of magnetic and electrical properties. Higher $Fe_3O_4$ leads to improved magnetic properties but reduced connectivity. Higher PEDOT:PSS reduces attachment but has higher current. This connection may be varied by using a stronger magnet, better interfacing etc. to boost the signal.

EXAMPLE 9. Magnetic Connections for Sensing

This example demonstrates that the magnetic connectors may be attached to a sensor in order to obtain readings without the use of any other connection.

Figure 8A:
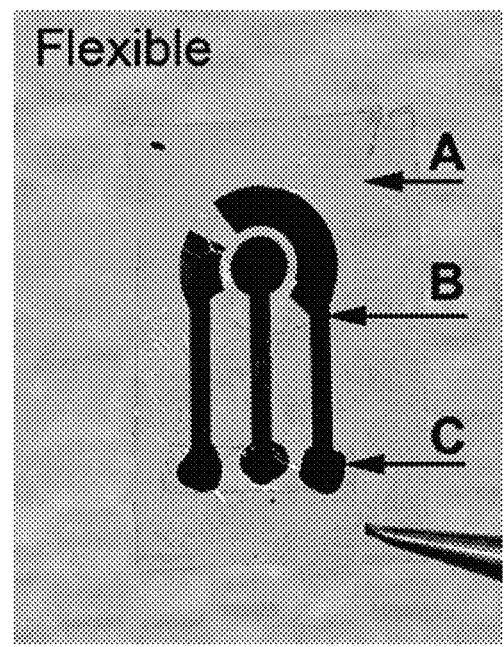
FIG. 8A and B. Schematic of microelectrode configurations showing the magnetic conductive ink used to make a magnetic and electrically conductive connection. A) flexible magnet on a flexible substrate; B) flexible magnet on a flexible substrate that has been immobilized on a rigid substrate (glass).
Figure 8B:
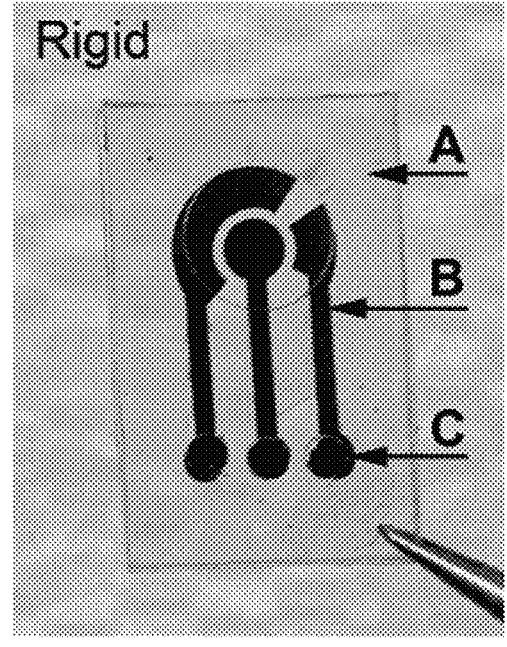

Exemplary microelectrode configurations are shown in FIG. 8A and B, where biodegradable conductive ink was used to form electrodes and the multifunctional (magnetic and conductive) ink was used to form nodes on the electrodes. The substrate is a flexible thin film substrate which can be, for example, silk protein, paper or textile. The thin film of FIG. 8A is shown supported on glass to form the rigid substrate of FIG. 8B. In FIGS. 8A and B, Arrow A indicates the substrate, Arrow B indicates the electrode formed from degradable conductive ink and Arrow C indicates the flexible magnets formed from magnetic conducting ink.

Figure 9A:
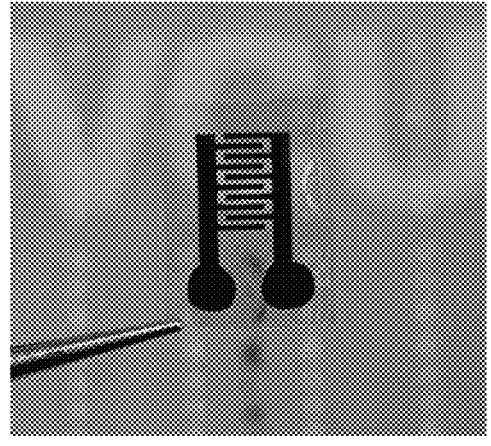
FIG. 9A and B. The inks may be dispensed on (A) flexible silk or (B) flexible paper substrates.
Figure 9B:
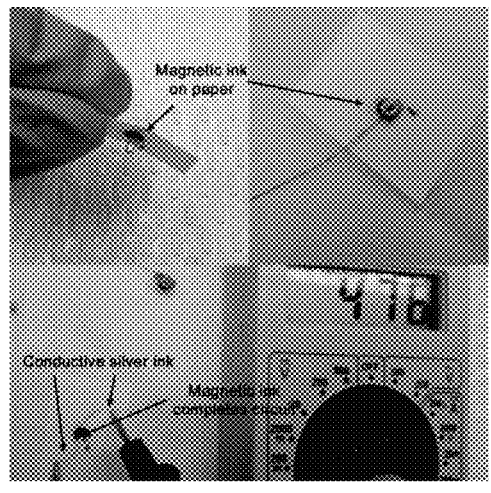

FIG. 9A and B shows formation of MCI nodes on electrodes on silk (A) and on paper (B).

Figure 10:
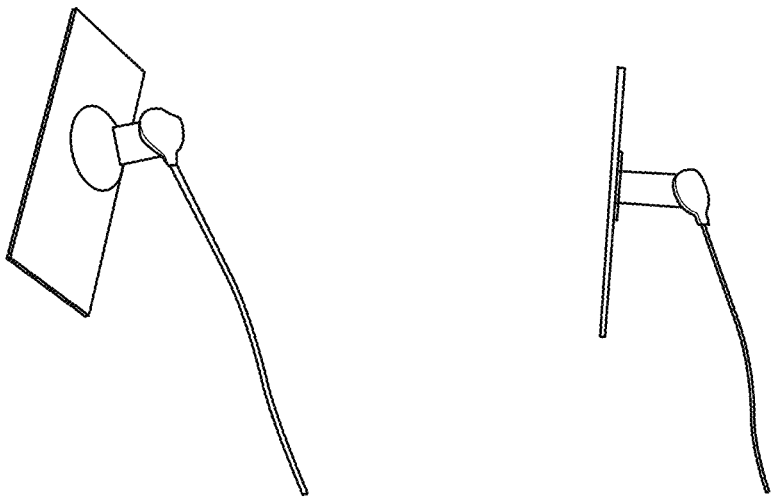
FIG. 10. Two views of a cover slip attached to a rigid neodymium (Nd) magnet using via a magnet formed from the MCI disclosed herein.

FIG. 10 shows successful use of the MCI to form a magnet on a glass slide. The connection between the MCI magnet and a Nd magnet is sufficient to hold the glass slide perpendicularly.

The magnetic connectors may be attached to a sensor in order to obtain readings (without the use of any other connection) (FIG. 11). The connection is temporary and reversible: as long as the magnet is in contact with the ink on the sensor, it is possible to get a reading. When the magnet is detached, the connection is lost. The magnets are strong Nd magnets with attached wiring and encased in a suitable extruded material such as plastic, epoxy, resin, or PDMS to form the connection device.

EXAMPLE 10. Surface Attachment Testing Using Surfaces of Different Compositions (Water Stability)

In order to prevent dissolution of the ink or smudging when wet, an adhesion promoter is added to the ink. Adhesion promoters enable the ink to become irreversibly impervious to water when dry. In this example, two different salts were tested from the commercial vendor Polyscope. Polyscope supplies hydrolyzed styrene maleic anhydride copolymers as sodium, potassium and ammonium salt solutions under the brand name XIRAN® SL. The stability of the magnetic ink on various polymer surfaces were tested. The composition of the base ink was the same but XIRAN® 1550H and 3000H was added to the composite in amounts of 2.5%, 5% and 10%. A slightly different procedure was followed in this trial wherein the XIRAN® additives were mixed for ~5 hrs. as compared to 1 hr. in the last trial. Example polymer surfaces were tested including polystyrene, PDMS, polyvinyl chloride, and 3D printed porous polymer. The ink was cast onto clean surfaces and dried under ambient conditions. The samples were immersed in water to test their water resistance and surface wettability. While the inks did not redissolve in the water, the adhesion to non-porous surfaces was not very strong. The ink detaches between 30 minutes and 1 hour from such surfaces. The magnetic connection ink is therefore extremely adhesive to porous surfaces including paper, silk and 3D printed porous polymers, but not necessarily to non-porous polymers.

EXAMPLE 11. This Example Describes Further Formulation and Characterization of the Multifunctional Conducting Ink (MCI) and its Use as a Transient Connector for Devices Version 4.0 of the ink comprised, in a stable water dispersion:
  i) iron oxide ($Fe_3O_4$) nanoparticles or magnetic iron oxide ($Fe_3O_4$) nanoparticles;

ii) nanoparticles of an exemplary conducting polymer (PEDOT:PSS);
  iii) an exemplary surfactant (Tween® 20);
  iv) an exemplary stabilizer (PEG 400); and
  v) an exemplary adhesion promoter (ammonium salt of styrene maleic anhydride).

These components together made the ink jettable or extrudable through a nozzle. The ink is indelible on drying on a substrate and may therefore be used in dry and wet environments.

An exemplary composition of the ink is presented in Table 1 below.

TABLE 1

| Component | Mass % | Volume % |
|---|---|---|
| Conducting polymer (PEDOT:PSS) | 40-45 | 50-55 |
| $Fe_3O_4$ nanoparticles | 8-10 | 28-35 |
| Solubilizer (e.g., PEG 400) | 4-5 | 4-5 |
| Surfactant (e.g., Tween 20) | 0.5-1 | 1 |
| Adhesion promoter (e.g., ammonium salt of styrene maleic anhydride) | 1-3 | 10 |

The components were selected and combined to provide the following properties to the ink:
  i) Stable water dispersion.
  ii) Physical and electronic contact to a device by means of a magnet. This may be used to facilitate on/off, transient connections.
  iii) Suitable viscosity and fluid properties to be dispensed through a nozzle in the form of dots, lines, or other patterns.
  iv) Adhesion to a variety of surfaces including silk, paper, polystyrene, and polydimethylsiloxane (PDMS). Printing was done at room temperature.
  v) Stability on drying: the ink and patterns made with the ink do not smudge, smear or wash off easily.

Electrochemical Characterization of the MCI

I-V characteristics of the ink were measured. The ink was cast on a cover slip with connections made using silver paste. Linear sweep voltammetry (LSV) was performed on the ink. A linear current was observed in the potential range of –1V to 1V with mA current. The results are shown in FIG. 12.

Electrical Connections Using MCI 4.0

Electrical connections made using MCI 4.0 were verified. The I-V curve of pure PEDOT: PSS (1% dispersion) film in the range of –1V to 1V was compared. The I-V curve obtained using the MCI 4.0 was stable without loss in electrical or magnetic properties over multiple connections. The results are shown in FIG. 13.

Figure 14C:
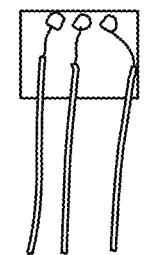
Figure 14D:
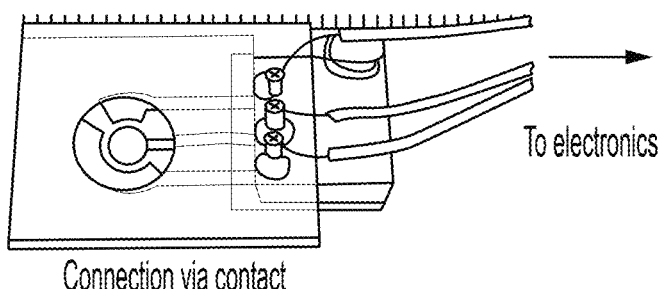

Using the MCI to Form a Connection to a Device: Exemplary Applications Using the MCI for Direct Connections to Devices One example is a biosensor with the interconnections formed using the MCI. An organic electrode is shown in FIG. 14B-D. MCI on the electrode ends is used to facilitate magnetic connections via a magnetic connector as shown. In contrast to conventional magnetic connectors (FIG. 14A), which have separate electrical (e.g., gold, non-magnetic) and physical e.g. (black, magnetic) elements, the ink provides both the electrical and physical connection to a magnet.

Use of the MCI to Form Transient Connections

Figure 15B:
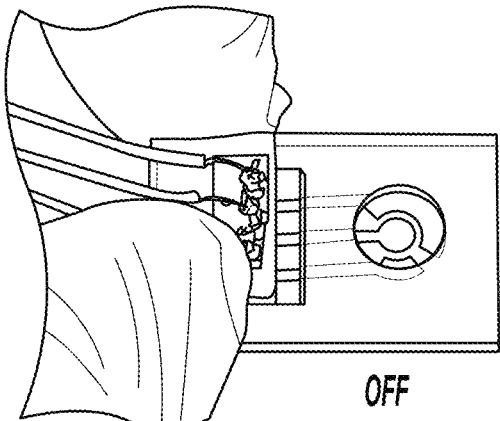

One application of the MCI is to enable transient connections via direct contact. These contacts are ON when the interconnect is placed on the ink (FIG. 15A) and OFF when withdrawn (FIG. 15B).

Linear scanning voltammetry (LSV) was performed while detaching and reattaching the magnetic connector before every run (FIG. 16A). Next, chronoamperometry was performed while attaching and detaching the magnetic connector to the sensor (FIG. 16B). The sensor gave a similar current output each time the connector was attached to the O3ES.

Use of the MCI to Connect to a Biosensor—Detection of Uric Acid

Detection of uric acid was carried out using a 3-electrode system with magnetic connection via MCI 4.0 and magnetic connector. The results are shown in FIGS. 17A-C. As can be seen, FIG. 17 A the response of a biosensor to successive additions of uric acid. The biosensor is connected using a magnetic connector similar to the one shown in FIG. 15A via nodes formed using the ink. FIG. 17B shows the calibration curve to uric acid. FIG. 17C shows the calibration curve in comparison to a conventional connection using silver paste. While the sensitivity is lower with the magnetic connection ink, the response is linear and quite competitive.

Another proposed embodiment of this system is in which one of the surfaces is a flexible magnet that can be placed on an irregular surface. This includes, but is not limited to, placement on plants, produce, skin, soft tissue, bone, etc. A flexible film or device can be placed on the surface and the nodes formed by the MCI permit an electrical connection as shown in FIG. 18A and B. The connection can be a two-way connection, permitting the transfer of signals to and from the surface on which the flexible magnet is placed.

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

REFERENCES

1. Taccola, S., et al., Characterization of free-standing PEDOT: PSS/iron oxide nanoparticle composite thin films and application as conformable humidity sensors. ACS applied materials & interfaces, 2013. 5(13): p. 6324-6332.
2. Kumar, S., et al., Electrochemical paper-based cancer biosensor using iron oxide nanoparticles decorated PEDOT: PSS. Analytica Chimica Acta, 2019. 1056: p. 135-145.
3. Muñoz-Bonilla, A., J. Sánchez-Marcos, and P. Herrasti, Magnetic nanoparticles-based conducting polymer nanocomposites. Conducting polymer hybrids, 2017: p. 45-80.

We claim:

1. An ink, comprising
conducting nanoparticles which are nanopolymers,
ferromagnetic nanoparticles,
an adhesion promoter,
an aqueous carrier, and optionally, one or both of a surfactant and a stabilizer,
wherein the conducting nanoparticles are separate from the ferromagnetic nanoparticles.

2. The ink of claim 1, where the conducting nanopolymers are PEDOT: PSS (poly(3,4-ethylenedioxythiophene) polystyrene sulfonate), polypyrrole or polyaniline nanopolymers.

3. The ink of claim 1, wherein the ferromagnetic nanoparticles are $Fe_2O_3$ and/or $Fe_3O_4$.

4. The ink of claim 1, wherein the conducting nanopolymers are PEDOT: PSS nanopolymers and the ferromagnetic nanoparticles are $Fe_3O_4$.

5. The ink of claim 1, wherein the adhesion promoter is a salt of a styrene maleic anhydride copolymer.

6. The ink of claim 1, wherein the stabilizer is a polyoxazoline, a poly(glycerol), a polyacrylamide, or a polyethylene glycol.

7. The ink of claim 1, wherein the ink is magnetic.

8. The ink of claim 1, wherein a ratio of the conductive nanoparticles to the ferromagnetic nanoparticles ranges from 1:1 to 1:3.

* * * * *